United States Patent [19]

Kaeding et al.

[11] Patent Number: 4,982,030

[45] Date of Patent: Jan. 1, 1991

[54] PROCESS FOR PREPARATION OF PARA-DIVINYLBENZENE

[75] Inventors: Warren W. Kaeding, Lawrenceville; John M. Klosek, Sewaren, both of N.J.; Philip J. Yannich, Jr., Lake Hill, N.Y.; Lewis B. Young, Skillman, N.J.

[73] Assignee: Mobil Oil Corporation, Fairfax, Va.

[21] Appl. No.: 376,918

[22] Filed: Jul. 3, 1989

Related U.S. Application Data

[63] Continuation of Ser. No. 151,739, Feb. 3, 1988, abandoned, which is a continuation-in-part of Ser. No. 15,575, Feb. 11, 1987, abandoned, which is a continuation of Ser. No. 759,191, Jul. 26, 1985, abandoned.

[51] Int. Cl.$^5$ ............................ C07C 2/28; C07C 7/14
[52] U.S. Cl. .................................... 585/323; 585/440; 585/469
[58] Field of Search ............... 585/323, 440, 441, 444, 585/445, 442, 469

[56] References Cited

U.S. PATENT DOCUMENTS

| | | | |
|---|---|---|---|
| 3,360,579 | 12/1967 | Hills et al. | 260/699 |
| 3,715,408 | 2/1973 | Brown et al. | 585/441 |
| 3,849,508 | 11/1974 | Van Tassell | 585/467 |
| 3,904,484 | 9/1975 | King | 585/445 |
| 4,009,217 | 2/1977 | Uitti | 585/445 |
| 4,117,024 | 9/1978 | Kaeding | 585/467 |
| 4,404,123 | 9/1983 | Chu | 252/463 |
| 4,417,084 | 11/1983 | Chu | 585/440 |
| 4,447,666 | 5/1984 | McWilliams | 585/467 |
| 4,503,163 | 3/1985 | Chu | 502/183 |
| 4,504,594 | 3/1985 | Chu | 502/184 |

FOREIGN PATENT DOCUMENTS

| | | | |
|---|---|---|---|
| 0217492 | 4/1987 | European Pat. Off. | |
| 83/00687 | 3/1983 | World Int. Prop. O. | 585/445 |

OTHER PUBLICATIONS

W. W. Kaeding, Sharp-Selective Reactions with Zeolite Catalysts V. Alkylation or Disproportionation of Ethylbenzene to Produce P-Diethylbenzene, from Journal of Catalysis, vol. 95, No. 2, Oct. 1985.

*Primary Examiner*—Asok Pal
*Attorney, Agent, or Firm*—Alexander J. McKillop; Charles J. Speciale; Edward F. Kenehan, Jr.

[57] ABSTRACT

There is provided a method for preparing para-divinylbenzene by dehydrogenating para-diethylbenzene followed by crystallizing para-divinylbenzene. The para-diethylbenzene may be prepared by alkylating ethylbenzene with ethylene in the presence of a para-selective molecular sieve catalyst, such as ZSM-5 modified with an oxide of magnesium and, optionally, an oxide of phosphorus.

20 Claims, No Drawings

PROCESS FOR PREPARATION OF PARA-DIVINYLBENZENE

CROSS-REFERENCE TO RELATED APPLICATION

This is a continuation of copending application Ser. No. 151,739, filed on Feb. 3, 1988, now abandoned, which is a continuation-in-part of copending U.S. application Ser. No. 015,575, filed Feb. 11, 1987, now abandoned, which is a continuation of U.S. application Ser. No. 759,191, filed July 26, 1985, now abandoned. The entire disclosures of these Ser. Nos. 015,575 and 759,191 are expressly incorporated herein by reference, now both abandoned.

BACKGROUND

This invention relates to a method for preparing para-divinylbenzene (PDVB) by dehydrogenating para-diethylbenzene (PDEB) followed by crystallization of para-divinylbenzene.

Divinylbenzene (DVB) is a very reactive monomer which may be used for polymers or as a crosslinking agent for copolymers. Divinylbenzene is presently available as a 40/60 para/meta mixture. This mixture is produced by dehydrogenation of the corresponding diethylbenzene (DEB) mixture. The latter can be produced by an alkylation with $AlCl_3/HCl$ to give all three diethylbenzene isomers.

Purification of this divinylbenzene mixture by distillation is impractical because of the high temperatures required and sensitivity to polymerization. Furthermore, these isomers cannot be separated by fractional crystallization, when in admixture in such proportions.

SUMMARY

In accordance with an aspect of the present invention, there is provided, a method for preparing para-divinylbenzene, said method comprising the steps of:

(i) contacting a feedstock comprising diethylbenzene with a dehydrogenation catalyst under sufficient dehydrogenation conditions, whereby para-diethylbenzene is dehydrogenated to form para-divinylbenzene;

(ii) maintaining the product of step (i) under sufficient crystallization conditions, whereby solid crystals of said para-divinylbenzene are formed in a mother liquor;

(iii) separating said crystals of para-divinylbenzene from said mother liquor; and (iv) recovering said crystals of para-divinylbenzene, wherein the proportion of the para-isomer of said diethylbenzene in the dehydrogenation step (i) is sufficient to enable the crystallization of para-divinylbenzene in step (ii) after said diethylbenzene is dehydrogenated. The diethylbenzene in step (i) may comprise, e.g., at least 90 percent, more particularly at least 95 percent, especially at least 98 percent, of the para-isomer.

In accordance with another aspect of the invention, there is provided a method for preparing para-divinylbenzene, said method comprising the steps of:

(i) alkylating ethylbenzene with ethylene under sufficient alkylation conditions over a para-selective alkylation catalyst comprising a molecular sieve, whereby hydrocarbons other than ethylene and ethylbenzene are produced, said other hydrocarbons comprising at least 70 percent by weight of diethylbenzene; said diethylbenzene comprising at least 90 percent of the para-isomer;

(ii) removing essentially all of the $C_8$ aromatics and hydrocarbons of lesser boiling point from the product stream of said alkylation step (i);

(iii) subjecting the remainder of the hydrocarbons after step (ii) to sufficient dehydrogenation conditions, whereby para-diethylbenzene is dehydrogenated to form para-divinylbenzene;

(iv) maintaining the product of step (iii) under sufficient crystallization conditions, whereby solid crystals of said para-divinylbenzene are formed in a mother liquor;

(v) separating said crystals of para-divinylbenzene from said mother liquor; and (vi) recovering said crystals of para-divinylbenzene.

EMBODIMENTS

The para-diethylbenzene containing feedstock may be supplied from a variety of sources. Preferably, the para-diethylbenzene in this feedstock may be prepared by alkylation of ethylbenzene with ethylene over a para-selective molecular sieve catalyst. Such an ethylation reaction is described in the Kaeding U.S. Pat. No. 4,117,024, the entire disclosure of which is expressly incorporated herein by reference. Note especially Examples 8 and 9 on columns 17-19 of this patent. Preferred ethylation catalysts comprise ZSM-5 modified with an oxide of magnesium and, optionally, an oxide of phosphorus. Such ZSM-5 may be prepared in accordance with the method of the Dwyer et al U.S. Pat. No. 4,375,458, the entire disclosure of which is expressly incorporated herein by reference, and may be modified with magnesium oxide in accordance with the procedure described in the McWilliams U.S. Pat. No. 4,447,666, the entire disclosure of which is expressly incorporated herein by reference.

Since the para-selectivity of ZSM-5 increases with crystal size, very large crystals of ZSM-5 may not need modification at all in order to produce a sufficient proportion of para-diethylbenzene to enable crystallization of para-divinylbenzene after the dehydrogenation step.

When ethylbenzene is alkylated with ethylene, especially in the presence of a catalyst containing ZSM-5, alkylation conditions may include a temperature of from about 340° C. to about 500° C., a pressure of from about atmospheric to about 200 atmospheres, a weight hourly space velocity of from about 2 to about 2000 and an ethylbenzene/ethylene mole ratio of from about 1/1 to 20/1.

In addition to ethylation of ethylbenzene over para-selective catalysts, the diethylbenzene for use in the dehydrogenation step of the present invention may be derived from a variety of other sources. For example, ethylbenzene may be disproportionated over a para-selective catalyst under sufficient disproportionation conditions. The Tassell U.S. Pat. No. 3,849,508, the entire disclosure of which is expressly incorporated herein by reference, describes the separation of para-diethylbenzene from a mixture of its isomers by selective adsorption on metal exchanged Y zeolites. High purity para-diethylbenzene has also been prepared by reduction of para-ethylacetophenone. Note the Hochwalt U.S. Pat. No. 2,390,368, the entire disclosure of which is expressly incorporated herein by reference.

The dehydrogenation catalyst used in step (i) may be any such dehydrogenation catalyst which is capable of achieving the desired degree of dehydrogenation without causing an undesired degree of side reactions, such as isomerization of alkyl groups on the benzene rings.

Examples of such dehydrogenation catalysts may comprise iron oxide, potassium carbonate, chromium compounds and various promoters. Such catalysts will not cause the undesired isomerization of alkyl groups during the dehydrogenation step.

When ethylbenzene is alkylated with ethylene over a para-selective zeolite catalyst, e.g. comprising ZSM-5, a hydrocarbon stream may be obtained which includes the diethylbenzene product, unreacted ethylbenzene, and various byproducts such as benzene, toluene, xylene, ethyltoluene and other aromatics. The unreacted ethylbenzene and lesser boiling hydrocarbons may be removed by simple distillation. It is not necessary to remove other aromatics such as ethyltoluene and meta-diethylbenzene from the product stream prior to the dehydrogenation step disclosed herein, whereby para-diethylbenzene is converted to para-divinylbenzene and para-ethylvinylbenzene.

The product of the dehydrogenation step disclosed herein may include a number of additional hydrocarbons in addition to para-divinylbenzene and para-ethylvinylbenzene. Examples of these additional hydrocarbons include unreacted diethylbenzene, as well as methylstyrene, ethyltoluene, xylene, ethylbenzene, toluene, benzene and various hydrocarbons having 11 or more carbon atoms. It is not necessary to remove any liquid hydrocarbons by a separate distillation treatment prior to conducting the crystallization step disclosed herein. Accordingly, the present hydrocarbon mixture from which para-divinylbenzene is crystallized (hereinafter also referred to as the crystallization mixture) may include, e.g. at least about 8 wt. % (e.g. at least 11 wt. %) of diethylbenzene, at least about 7 wt. % (e.g. at least 9 wt. %) of methylstyrene and at least about 2 wt. % (e.g. at least 3 wt. %) of ethyltoluene. This crystallization mixture may comprise at least about 20 wt. % (e.g. at least 25 wt. %) of the sum of diethylbenzene plus other hydrocarbons having 9 or less carbon atoms. The amount of para-divinylbenzene in this crystallization mixture may be, e.g. 50 wt. % or less. Given the nature and amount of impurities in the crystallization mixture, it was particularly surprising that para-divinylbenzene could be crystallized directly therefrom, without first subjecting the mixture to conditions such as vacuum distillation sufficient to remove such impurities from the crystallization mixture. The crystals of para-divinylbenzene obtained by the present process may be exceptionally pure, e.g., having a para-divinylbenzene content of at least 98 percent by weight.

EXAMPLE 1

Ethylbenzene is alkylated with ethylene, over a para-selective zeolite catalyst, to produce high concentrations of the para isomer in the diethylbenzene product. A representative example of results with magnesium modified ZSM-5 zeolite catalyst containing an alumina binder is shown in Table 1. The catalyst was regenerated with hydrogen, overnight, to restore initial activity. Diethylbenzene is the major product, 75 to 86 percent selectivity. The para isomer in the diethylbenzene product ranged from 97.8 percent to 98.8 percent. Disproportionation of ethylbenzene also gave para-diethylbenzene and benzene. The benzene by-product can be recycled to make more ethylbenzene starting material.

TABLE 1

| Alkylation of Ethylbenzene (EB) with Ethylene Conditions: Temp. 425° C.; pressure 100 psig; WHSV EB 30.3, $C_2H_4$ 1.7, $H_2$ 0.25; mole ratio EB/$C_2H_4$/$H_2$ 6.9/1.0/2.9; Mg-ZSM-5 catalyst | | | | | | | | | | | |
|---|---|---|---|---|---|---|---|---|---|---|---|
| Run | 1 | 3 | 5 | 8 * | 9 | 12 | 16 | 17 | 21 | 23 | 26 |
| TOS, hrs | .1 | 3 | 20 | 27 | 28 | 32 | 36 | 52 | 60 | 78 | 84 |
| Conv. EB % | 20.6 | 18.3 | 14.7 | 14.1 | 21.1 | 18.8 | 17.1 | 14.8 | 12.9 | 9.6 | 8.6 |
| $C_2H_4$ | 71.7 | 73.5 | 68.6 | 55.2 | 76.2 | 70.0 | 68.6 | 62.7 | 54.1 | 38.4 | 35.1 |
| Selectivity, wt % | | | | | | | | | | | |
| Benzene | 15.0 | 13.7 | 11.6 | 11.5 | 17.1 | 13.5 | 12.5 | 10.6 | 9.5 | 7.2 | 6.9 |
| Toluene | .8 | .5 | .3 | .3 | .9 | .5 | .4 | .3 | .2 | .2 | 0 |
| XYL, ET | 3.0 | 2.9 | 2.9 | 3.0 | 3.1 | 2.8 | 2.8 | 2.9 | 3.1 | 3.8 | 4.1 |
| DEB | 74.2 | 78.7 | 81.9 | 81.9 | 73.7 | 79.0 | 80.2 | 81.9 | 83.8 | 95.4 | 85.5 |
| Other Arom | 2.0 | 1.7 | 1.3 | 1.0 | 2.3 | 1.7 | 1.4 | 1.2 | 1.0 | .8 | 0 |
| Gas | 3.5 | 1.3 | .7 | .8 | 1.3 | 1.2 | .9 | 1.5 | .6 | .6 | .5 |
| $C_5$-$C_9$ | 1.5 | 1.2 | 1.3 | 1.5 | 1.6 | 1.4 | 1.8 | 1.6 | 1.8 | 2.0 | 3.0 |
| Total | 100.0 | 100.0 | 100.0 | 100.0 | 100.0 | 100.0 | 100.0 | 100.0 | 100.0 | 100.0 | 100.0 |
| % Para | 97.8 | 98.1 | 98.5 | 98.5 | 98.0 | 98.4 | 98.5 | 98.5 | 98.6 | 98.8 | 98.8 |

*Catalyst regenerated with hydrogen overnight, 16 hrs.

EXAMPLE 2

The 98+ percent para-diethylbenzene is dehydrogenated to produce para-ethylvinylbenzene and para-divinylbenzene and hydrogen. Alkaline dehydrogenation catalysts containing iron oxide, potassium carbonate, chromium compounds and promoters are used.

Formulations containing iron oxide (45-54 percent), potassium oxide (43-50 percent), and chromium oxide (2.5-3.5 percent), by weight, are especially effective. Addition of 2 to 5 percent amounts of other promoters also gives enhanced selectivity. Bismuth oxide (2-5 percent) increases activity and selectivity. Combinations of calcium oxide and bismuth oxide or calcium oxide and gallium oxide give very high selectivities at moderate conversions. In general catalysts effective for dehydrogenation of p-ethyltoluene to p-methylstyrene are effective for production of para-divinylbenzene. Such dehydrogenation catalysts are discussed in the Chu U.S. Pat. Nos. 4,404,123; 4,503,163; and 4,504,594, the entire disclosures of which are expressly incorporated herein by reference.

A representative dehydrogenation mixture of liquid products is summarized in Table 2. The alkyl groups are not isomerized during the dehydrogenation step. The corresponding vinyl products, therefore, contain the same isomeric mixtures. By varying the reaction severity, the ratio of para-ethylvinylbenzene and para-divinylbenzene can be changed. Higher temperatures (620°-630° C.), and contact times plus increased water/hydrocarbon feed ratios favor para-divinylbenzene. Lower severities (590°-620° C.), etc., favor para-ethylvinylbenzene.

Small amounts of stabilizers (50-400 ppm), such as tert-butylcatechol (TBC), are effective for inhibiting polymerization and decomposition of these reactive monomers during handling and purification. In addition, insoluble, undesired popcorn polymers may be prevented by the use of small amounts of H$_2$S according to the methods described by C. Chu in U.S. Pat. No. 4,417,084, the entire disclosure of which is expressly incorporated herein by reference.

TABLE 2

| Liquid Dehydrogenation Product Temp. 618° C. | |
|---|---|
| Compound | Weight Percent |
| Benzene | 0.2 |
| Toluene | .8 |
| Ethylbenzene | .6 |
| P-Xylene | .2 |
| Ethyltoluene, para | 3.4 |
| Ethyltoluene, meta | 1.3 |
| Diethylbenzene, para | 11.3 |
| Diethylbenzene, meta | .2 |
| Methylstyrene, para | 10.0 |
| Methylstyrene, meta | .1 |
| Ethylvinylbenzene, para | 22.7 |
| Ethylvinylbenzene, meta | .5 |
| Divinylbenzene, para | 47.7 |
| Divinylbenzene, meta | .7 |
| Other | .3 |
| Total | 100.0 |

Additional information on reaction conditions are summarized in Table 3. In this case, para-divinylbenzene was the major product.

TABLE 3

| Dehydrogenation of P-Diethylbenzene (PDEB) to P-Divinylbenzene (PDVB) Conditions: Temp. 620° C.; LHSV 1.1 | | | | | | | | | | |
|---|---|---|---|---|---|---|---|---|---|---|
| Run | 1 | 2 | 3 | 4 | 1-4 AV. | 5 | 6 | 7 | 8 | 5-8 AV. |
| TOS, hrs. | 5 | 7.5 | 24 | 29 | — | 31 | 33 | 50 | 51 | — |
| Conv. PDEB, wt % | 83 | 86 | 86 | 87 | 85.5 | 86 | 84 | 75 | 75 | 80.0 |
| Steam/PDEB, wt ratio | 3.5 | 3.5 | 3.5 | 3.5 | 3.5 | 2 | 2 | 2 | 2 | 2 |
| Products, wt % | | | | | | | | | | |
| H$_2$, C$_2$-C$_7$ | 13.0 | 14.7 | 14.6 | 15.1 | 14.4 | 17.1 | 13.9 | 9.1 | 9.0 | 12.3 |
| PDEB | 16.7 | 13.9 | 14.3 | 13.4 | 14.6 | 13.8 | 16.0 | 24.8 | 24.8 | 19.8 |
| PEVB | 26.8 | 25.6 | 25.9 | 25.7 | 26.0 | 28.8 | 30.4 | 30.7 | 31.0 | 30.2 |
| PDVB | 43.4 | 45.6 | 45.1 | 45.6 | 44.9 | 40.2 | 39.4 | 35.2 | 35.0 | 37.5 |
| C$_{11+}$ | .1 | .2 | .1 | .2 | .1 | .1 | .3 | .2 | .2 | .2 |
| Total | 100.0 | 100.0 | 100.0 | 100.0 | 100.0 | 100.0 | 100.0 | 100.0 | 100.0 | 100.0 |

Separation, purification and recycle are important components of a useful process. In this instance, the ability to start with 98+ percent para-diethylbenzene provides some unique opportunities. Virtually all of the meta isomers are absent. After the dehydrogenation step, the desired para-divinylbenzene is present in relatively high concentration and crystallizes as pure white needles, mp 31°-32° C. The substantial presence of meta isomers prevents this. This very active monomer, para-divinylbenzene, is separated and purified by reducing the temperature.

This is in sharp contrast with the present commercial process for commercial divinylbenzene. This product contains approximately a 2/1 meta/para mixture. Heating is used to remove as much of the lower boiling products as possible. It is, however, impractical to provide a product with greater than 80 percent divinylbenzene purity. These monomers are simply too reactive to survive extended heating.

The present commercial product is, therefore, composed of a meta/para mixture determined by the initial composition of the diethylbenzene. It contains some unreacted diethylbenzene, ethylvinylbenzene and divinylbenzene.

Crystallization of the present para-divinylbenzene may take place in the presence or absence of added liquids. For example, judicious use of solvents may also be used to induce and promote crystallization. Pentane or petroleum ethers are effective and may be easily separated by distillation from the mother liquor.

If desired, the mother liquor remaining after removal of pure para-divinylbenzene may be distilled under vacuum to remove the para-ethylstyrene (PES) as a product. Alternatively, it may be recycled with the para-diethylbenzene starting material and converted to more para-divinylbenzene.

What is claimed is:

1. A method for preparing para-divinylbenzene, said method comprising the steps of:
   (i) alkylating ethylbenzene with ethylene under sufficient alkylation conditions over a para-selective alkylation catalyst comprising a molecular sieve, whereby hydrocarbons other than ethylene and ethylbenzene are produced, said other hydrocarbons comprising at least 70 percent by weight of diethylbenzene; said diethylbenzene comprising at least 90 percent of the para-isomer;
   (ii) removing essentially all of the C$_8$ aromatics and hydrocarbons of lesser boiling point from the product stream of said alkylation step (i);
   (iii) subjecting the remainder of the hydrocarbons after step (ii) to sufficient dehydrogenation conditions, whereby para-diethylbenzene is dehydrogenated to form para-divinylbenzene and para-ethylvinylbenzene;
   (iv) maintaining the product of step (iii) under sufficient crystallization conditions, whereby solid crystals of said para-divinylbenzene are formed in a mother liquor wherein the dehydrogenated product of step (i) is not subjected to distillation to remove diethylbenzene and/or hydrocarbons having 11 or more carbon atoms prior to said crystallization;
   (v) separating said crystals of para-divinylbenzene from said mother liquor; and
   (vi) recovering said crystals of para-divinylbenzene, wherein said product of step (iii), which is subjected to crystallization conditions in accordance with step (iv), comprises at least about 8 wt. % of diethylbenzene.

2. A method according to claim 1, wherein said diethylbenzene in said alkylation step (i) comprises at least 95 percent of the para-isomer.

3. A method according to claim 1, wherein said diethylbenzene in said alkylation step (i) comprises at least 98 percent of the para-isomer.

4. A method according to claim 3, wherein said molecular sieve is ZSM-5.

5. A method according to claim 4, wherein said ZSM-5 is modified with magnesium oxide.

6. A method according to claim 5, wherein said ZSM-5 is also modified with phosphorus oxide.

7. A method according to claim 1, wherein para-ethylstyrene is separated from the dehydrogenated product, and said para-ethylstyrene is recycled for further dehydrogenation along with para-diethylbenzene in accordance with dehydrogenation step (iii).

8. A method according to claim 1, wherein the weight ratio of para-divinylbenzene to para-ethylvinylbenzene produced in accordance with said dehydrogenation step (iii) is at least 35:31.

9. A method according to claim 1, wherein the dehydrogenation temperature in said dehydrogenation step (iii) is 620°–630° C.

10. A method according to claim 1, wherein said dehydrogenation catalyst of step (iii) contains 45–54 wt. % iron oxide, 43–50 wt. % potassium oxide and 2.5–3.5 wt. % chromium oxide.

11. A method according to claim 1, wherein at least 75 percent by weight of said para-diethylbenzene is converted in said dehydrogenation step (iii).

12. A method according to claim 1, wherein pentane or petroleum ether is added to the product of step (iii) prior to forming said crystals according to step (iv).

13. A method according to claim 1, wherein said crystals of para-divinylbenzene have a melting point of 31°–32° C.

14. A method according to claim 1, wherein said crystals of para-divinylbenzene are in the form of white needles.

15. A method according to claim 1, wherein said product of step (iii), which is subjected to crystallization conditions in accordance with step (iv), comprises at least about 7 wt. % of methylstyrene and at least about 2 wt. % of ethyltoluene.

16. A method according to claim 1, wherein said product of step (iii), which is subjected to crystallization conditions in accordance with step (iv), comprises at least about 11 wt. % of diethylbenzene, at least about 9 wt. % of methylstyrene and at least about 3 wt. % of ethyltoluene.

17. A method according to claim 15, wherein said product of step (iii), which is subjected to crystallization conditions in accordance with step (iv), comprises 50 wt. % or less of para-divinylbenzene.

18. A method according to claim 15, wherein said product of step (iii), which is subjected to crystallization conditions in accordance with step (iv), comprises at least about 20 wt. % of the sum of diethylbenzene plus other hydrocarbons having 9 or less carbon atoms.

19. A method according to claim 17, wherein said product of step (iii), which is subjected to crystallization conditions in accordance with step (iv), comprises at least about 25 wt. % of the sum of diethylbenzene plus other hydrocarbons having 9 or less carbon atoms.

20. A method according to claim 1, wherein said crystallization conditions of step (iv) comprise reducing the temperature of the product of step (iii) in the absence of added pentane or petroleum ether.

* * * * *